(12) United States Patent
Tijssen et al.

(10) Patent No.: US 11,147,707 B2
(45) Date of Patent: Oct. 19, 2021

(54) FLUID WARMING APPARATUS

(71) Applicant: THE SURGICAL COMPANY INTERNATIONAL B.V., Amersfoort (NL)

(72) Inventors: Peter Tijssen, Amersfoort (NL); Robertus Gerardus Van Oudenallen, Amersfoort (NL); Jasper Keuning, Amersfoort (NL); Bert Van Den Berg, Amersfoort (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 0 days.

(21) Appl. No.: 15/641,541

(22) Filed: Jul. 5, 2017

(65) Prior Publication Data

US 2018/0008456 A1    Jan. 11, 2018

(30) Foreign Application Priority Data

Jul. 7, 2016  (EP) .................................... 16178448

(51) Int. Cl.
*A61F 7/00*    (2006.01)
*A61F 7/02*    (2006.01)
(Continued)

(52) U.S. Cl.
CPC ............ *A61F 7/0097* (2013.01); *A61B 90/17* (2016.02); *A61F 7/0085* (2013.01); *A61F 7/02* (2013.01); *A61F 7/08* (2013.01); *H05B 1/02* (2013.01); *H05B 1/0272* (2013.01); *H05B 1/0297* (2013.01); *A61F 2007/006* (2013.01);
(Continued)

(58) Field of Classification Search
CPC ...... A61F 2007/0054; A61F 2007/0055; A61F 2007/006; A61F 2007/0071; A61F 2007/0072; A61F 2007/0086; A61F 2007/0093; A61F 2007/0095; A61F 2007/0096; A61F 7/007; A61F 7/0085; A61F 7/0097; A61F 7/02; A61F 7/08; H05B 1/00; H05B 1/02; H05B 1/0244; H05B 1/025; H05B 1/0269; H05B 1/0272; H05B 1/0297
See application file for complete search history.

(56) References Cited

U.S. PATENT DOCUMENTS 3,620,068 A    11/1971  Cary et al.
6,440,157 B1    8/2002  Shigezawa et al.
(Continued)

FOREIGN PATENT DOCUMENTS

JP        2004-124310        4/2004

*Primary Examiner* — Kaitlyn E Smith
*Assistant Examiner* — Bradford C. Blaise
(74) *Attorney, Agent, or Firm* — Nixon & Vanderhye P.C.

(57) ABSTRACT

The invention provides fluid warming apparatus comprising: a fan; a heater, the fan and the heater being configured to generate a heated fluid flow having a principle flow direction and an inhomogeneous temperature distribution in a distribution direction perpendicular to the said principle flow direction; and a plurality of temperature sensors offset from each other in the said distribution direction, wherein at least two of the temperature sensors are configured to measure temperatures of respective portions of the heated fluid flow having different temperatures.

18 Claims, 4 Drawing Sheets

(51) Int. Cl.
  *A61F 7/08* (2006.01)
  *H05B 1/02* (2006.01)
  *A61B 90/17* (2016.01)

(52) U.S. Cl.
  CPC .............. *A61F 2007/0055* (2013.01); *A61F 2007/0072* (2013.01); *A61F 2007/0086* (2013.01); *A61F 2007/0093* (2013.01); *A61F 2007/0095* (2013.01); *A61F 2007/0096* (2013.01); *A61F 2007/0233* (2013.01)

(56) References Cited

U.S. PATENT DOCUMENTS

| | | |
|---|---|---|
| 6,876,884 B2 | 4/2005 | Hansen et al. |
| 2009/0143844 A1* | 6/2009 | Cazzini ................ A61F 7/0097 607/104 |
| 2010/0286754 A1 | 11/2010 | Bly |
| 2014/0046412 A1 | 2/2014 | Officier |
| 2014/0343639 A1* | 11/2014 | Hopper ................ A61F 7/0085 607/104 |

\* cited by examiner

Fig. 4 ial measurement of the temperature of the heated air
flow generated by the fan and the heater.

FLUID WARMING APPARATUS

This application claims priority to EP 16178448.3 filed Jul. 7, 2016, the entire contents of which are hereby incorporated by reference.

FIELD OF THE INVENTION

The invention relates to: fluid warming apparatus; a patient temperature regulation system comprising a fluid warming apparatus; and a method of warming fluid.

BACKGROUND TO THE INVENTION

Devices used for forced air warming typically consist of a fan and a heater to generate a flow of heated air and a temperature regulation mechanism for controlling the temperature of the heater and thus of the heated air flow. The heater is typically provided downstream of the fan to maximise thermal efficiency. The heated air flow is applied to a patient via a hose and a perforated blanket which is draped over a patient's body. Openings in the blanket cause the heated air to exit the blanket onto the patient, thereby heating the patient by forced convection. To ensure that the air which is supplied to the patient is at the correct temperature, the temperature regulation mechanism requires an accurate measurement of the temperature of the heated air flow generated by the fan and the heater.

It is typical for the heaters of such devices to comprise a plurality of resistive heating elements spaced from each other, in which case air which comes into contact with the heating elements is heated more than air flowing through the gaps between adjacent heating elements without contacting them, which remains relatively unheated (although some heating by thermal radiation will take place). This causes the heated air flow generated by the fan and the heater to have an inhomogeneous temperature distribution along the direction in which the heating elements are spaced. Measuring the temperature of the heated air flow close to the heater is subject to significant error as it is unclear whether the temperature sensor is provided in a portion of the air flow which has been heated or in a portion which has been relatively unheated. In addition, regardless of which portion of the air flow is measured, the measured temperature is not necessarily representative of the temperature of the air which will be incident on the patient (because the hot and cool portions of the air flow have not yet mixed). As the heated air flow moves further from the heater, it mixes, thereby making the temperature distribution more homogeneous. In order to obtain a more accurate measurement of the temperature of the heated air flow, temperature measurements may be made far downstream of the heater where the temperature distribution of the heated air flow is more homogeneous. The further from the heater the sensors are placed, the more homogeneous the air temperature is.

To provide the heated air flow with a stable temperature, the temperature regulation mechanism must be able to react quickly to changes in circumstances. For example, if there is a sudden blockage to the air flow at the end of the hose, air is prevented from flowing out of the hose. If the heater remains on, the air trapped between the heater and the blockade continues to be heated, which can unintentionally increase the temperature of the air provided to the patient. To prevent this, the temperature measurement system must be able to quickly detect changes in the temperature of the stream of heated air generated by the fan and the heater, so that the temperature regulation mechanism can responsively reduce the quantity of heat produced by the heater if required. However, in forced air warmers in which temperature is measured far downstream of the heater and the fan (where the temperature distribution of the heated air flow is more homogeneous), it is not possible to quickly detect changes in temperature because of the time it takes for a change in temperature of the heated air flow generated by the fan and the heater to affect the downstream portion of the airflow where temperature is measured.

In some forced air warming devices, the heater is placed before the fan such that the fan helps to mix the heated air portions with relatively unheated air portions. This results in a heated air flow with a more homogeneous temperature distribution. However, because some of the heat generated by the heater heats up components provided between the heater and the temperature sensors (e.g. the fan), the temperature sensors cannot quickly detect changes in the temperature of heated air flow generated by the fan and the heater, and thermal efficiency is low.

Accordingly, a new way of measuring temperature in such devices is required which is accurate and which can react quickly to changes in circumstances.

SUMMARY OF THE INVENTION

A first aspect of the invention provides a fluid (typically gas, typically air) warming apparatus comprising: a fan; a heater, the fan and the heater being configured to generate a heated fluid flow (typically a heated air flow) having a principle flow direction and an inhomogeneous temperature distribution in a distribution direction perpendicular to the said principle flow direction; and a plurality of temperature sensors offset (and typically spaced) from each other in the said distribution direction, wherein at least two (preferably at least three, preferably each) of the temperature sensors are configured to measure temperatures of respective portions of the heated fluid flow having different temperatures (in use).

Typically the fluid warming apparatus is configured in use to provide an input fluid flow to a temperature regulation tool (e.g. a forced air warming tool such as a forced air warming blanket) which uses the input fluid flow to adjust or maintain a temperature of a subject (such as a human patient). The input fluid flow to the temperature regulation tool typically comprises fluid from the heated fluid flow which has mixed. Therefore the input fluid flow to the temperature regulation tool typically has a more homogeneous temperature distribution in the distribution direction than the heated fluid flow. Due to the inhomogeneous temperature distribution of the said heated fluid flow in the said distribution direction, the temperature measurements of the individual temperature sensors are not necessarily indicative of the heated fluid flow as a whole or indeed of the temperature of the said input fluid flow. By providing at least two temperature sensors configured to measure temperatures of respective portions of the heated fluid flow having different temperatures, temperature measurement data more indicative of the temperature of the heated fluid flow as a whole can be obtained. This allows the temperature of the input fluid flow received by the temperature regulation tool to be more accurately predicted and/or regulated. In addition, the temperature sensors can be provided closer to the heater because it is not necessary for the said heated fluid flow to have physically mixed to obtain a more homogeneous temperature distribution before temperature can be accurately determined. This results in a faster (and reliable) detection of a temperature change in the heated fluid flow generated by the fan and the heater compared to existing fluid warming apparatuses which require the heated fluid flow to mix before a reliable temperature reading can be obtained.

It may be that the patient temperature regulation tool comprises a blanket, a garment or an underbody (e.g. mattress) configured to regulate the temperature of the patient by forced convection. It may be that the patient temperature regulation tool comprises a pressure chamber having an air impermeable surface on a first side remote from the patient and an air permeable surface on a second side opposite the first side and facing the patient. It may be that the air impermeable surface has a port extending therethrough and configured to receive heated, pressurised air from the forced air warming apparatus. It may be that the air permeable surface allows the passage of air therethrough onto the patient (e.g. by way of openings or perforations). Typically the heated fluid flow comprises a relatively hot fluid flow portion and a relatively cool fluid flow portion, the relatively hot fluid flow portion having a (typically mean) temperature greater than a (typically mean) temperature of the relatively cool fluid flow portion. Typically at least one of the said temperature sensors is configured to measure a temperature of the relatively hot fluid flow portion and at least a different one of the temperature sensors is configured to measure a temperature of the relatively cool fluid flow portion.

Typically the fluid warming apparatus further comprises a controller configured to receive temperature measurements from the said temperature sensors. Typically the controller is configured to provide an output taking into account (typically responsive to) the temperature measurements from the said temperature sensors. Typically the said heated fluid flow is a first heated fluid flow and the output relates to a second heated fluid flow downstream of the first heated fluid flow (typically with respect to the principle flow direction of the heated fluid flow). For example, it may be that the output comprises a predicted temperature of the second heated fluid flow. Additionally or alternatively it may be that the output comprises a signal for regulating a temperature of the second heated fluid flow.

Accordingly, it may be that the heated fluid flow is a first heated fluid flow, and the apparatus further comprises a controller configured to predict and/or regulate a temperature of a second heated fluid flow downstream of the first heated fluid flow taking into account (typically responsive to) the temperatures measured by the said temperature sensors.

It may be that the controller does not explicitly predict the temperature of a second heated fluid flow downstream of the first heated fluid flow taking into account (typically responsive to) the temperatures measured by the said temperature sensors. In this case, it may be that the controller is configured to regulate a temperature of a second heated fluid flow downstream of the first heated fluid flow taking into account (typically responsive to) the temperatures measured by the said temperature sensors by using predetermined calibration data (e.g. obtained from a look-up table stored in a memory in communication with the controller). For example, the predetermined calibration data may comprise a plurality of predetermined calibration data portions, each of which comprises one or more control parameters associated with temperatures measured by one or more (or each) of the temperature sensors. It may be that the controller is configured to select a predetermined calibration data portion from the predetermined calibration data responsive to the temperatures measured by the said temperature sensors and to apply the control parameter(s) from the selected predetermined calibration data portion to regulate the temperature of the second heated fluid flow.

Typically the second heated fluid flow is derived from the first heated fluid flow. Typically the second heated fluid flow comprises fluid from the first heated fluid flow. Typically the second heated fluid flow comprises fluid from a first portion of the first heated fluid flow which has mixed together with fluid from a second portion of the first heated fluid flow having a different temperature from the first portion of the first heated fluid flow. Typically the second heated fluid flow has a more homogeneous temperature distribution (typically in the distribution direction) than the first heated fluid flow.

Typically the controller is configured to provide the said output taking into account a fluid velocity profile (i.e. a variation in fluid velocity) of the (first) heated fluid flow (typically in the distribution direction). Typically the controller is configured to predict and/or regulate the temperature of the second heated fluid flow taking into account a fluid velocity profile of the (first) heated fluid flow (typically in the distribution direction).

It may be that the controller is configured to predict and/or regulate the temperature of the said second fluid flow taking into account the fluid velocity profile of the heated fluid flow by weighting the said temperatures measured by the temperature sensors in accordance with respective predetermined (e.g. calibration) weightings (e.g. weightings associated with the respective temperature sensors). It may be that the controller is further configured to sum the weighted temperature measurements and divide the sum by the number of temperature sensors.

Typically the weightings applied to the temperatures measured by each of two or more of the temperature sensors are different from each other. It may be that the predetermined weightings are adjustable.

Typically the fluid warming apparatus further comprises at least one further temperature sensor configured to measure a temperature of a fluid (e.g. air) intake (e.g. ambient air) and wherein the controller is configured to predict and/or regulate the temperature of the second heated fluid flow taking into account (e.g. responsive to) the measured temperature of the fluid intake.

It will be understood that the temperature of the fluid intake is typically representative of an environmental temperature external to the fluid warming apparatus.

It may be that the controller is configured to regulate the temperature of the second heated fluid flow by adjusting one or more properties of the heater and/or the fan taking into account (e.g. responsive to) the temperatures measured by the said temperature sensors. For example, it may be that the controller is configured to adjust a heat output by the heater taking into account (e.g. responsive to) the temperatures measured by the said temperature sensors. Additionally or alternatively the controller may be configured to adjust a rotational speed of the fan taking into account (e.g. responsive to) the temperatures measured by the said temperature sensors.

It may be that the controller is configured to predict the temperature of the second heated fluid flow taking into account the said temperature measurements from the said temperature sensors. It may be that the controller is configured to regulate the temperature of the second heated fluid flow (e.g. by adjusting one or more properties of the heater and/or the fan) responsive to the predicted temperature of the second heated fluid flow.

Typically the controller is configured to regulate the temperature of the second heated fluid flow in accordance with a (typically predetermined) target temperature.

The target temperature may be between 40° C. and 50° C., more typically between 42° C. and 48° C., even more typically between 43° C. and 47° C. It may be that the target temperature is 43° C. It may be that the target temperature is 45° C.

It will be understood that the controller can react (e.g. by adjusting the heat output by the heater) more quickly (and accurately) to changes in temperature of the (first) heated fluid flow caused by changes in circumstances (e.g. the controller can better prevent the heater from overheating the (first) heated fluid flow, for example, in the event of a sudden blockade of the output fluid flow from the fluid warming apparatus) because of the faster (and reliable) detection of the temperature change.

It may be that the fluid warming apparatus further comprises a hose in fluid communication with the first heated fluid flow, wherein the second heated fluid flow is carried by the hose or provided downstream of the hose. Typically the hose is configured to fluidly connect the (first) heated fluid flow with a temperature regulation tool. It may be that the second heated fluid flow is a heated fluid flow at an output of the hose. It may be that the second heated fluid flow is a heated fluid flow derived from a heated fluid flow output by the hose.

Typically the controller comprises a computer processing system comprising a computer processor. It may be that the controller comprises two or more computer processors, for example comprising a first computer processor for controlling the heat output of the heater and a second computer processor for controlling the fan speed. Typically in this case each said processor is configured to receive temperature measurements from the temperature sensors and to provide an output responsive thereto. It may be that the said computer processors are in communication with each other. The controller may be implemented in software or hardware or in a combination of both software and hardware.

Alternatively, the controller may be implemented in analog electronics. It may be that the controller comprises first analog circuitry for controlling the heat output of the heater (typically responsive to the said temperature measurements) and second analog circuitry for controlling the fan speed (typically responsive to the said temperature measurements).

The fluid warming apparatus may further comprise a safety temperature sensor (typically different from the said temperature sensors, although the sensors may be of the same type) configured to measure a temperature of the heated fluid flow to provide a safety temperature measurement. The fluid warming apparatus may further comprise a safety controller (typically different from the said controller, although the controllers may be of the same type) configured to receive temperature measurements from the safety temperature sensor and to reduce the output of, or switch off, the heater and/or the fan responsive to the safety temperature measurement exceeding a threshold.

Typically the temperature sensors are configured to measure the temperatures of the respective portions of the (first) heated fluid flow by measuring a (typically electrical) parameter (e.g. electrical resistance) indicative of temperature.

Typically the controller is in (typically electrical, in some embodiments wired and in other embodiments wireless) communication with the temperature sensors such that the controller receives temperature measurements from the said temperature sensors.

Typically each of the temperature sensors is configured to measure the temperature of the respective portion of the (first) heated fluid flow independently of the other temperature sensors.

Typically the heater comprises a plurality of (typically electrically resistive or Joule) heating elements offset (and typically spaced) from each other in the said distribution direction.

Typically the heating elements comprise electrical conductors having longitudinal axes extending in a direction perpendicular to the distribution direction (and typically perpendicular to the principle direction of flow).

Typically the temperature sensors are distributed in the said distribution direction differently from the distribution of the heating elements in the said distribution direction.

Typically one or more or each of the heating elements has (have) a different extent in the said distribution direction than one or more or each of the temperature sensors. For example, one or more or each of the temperature sensors has (have) a greater extent in the said distribution direction than one or more or each of the heating elements. Typically one or more or each of the temperature sensors has a greater surface area (which is responsive to temperature) than a cross sectional area perpendicular to its longitudinal axis of one or more or each of the heating elements. It may be that each of one or more (or indeed each) of the temperature sensors cover respective portions of the (first) heated fluid flow having different temperatures. In this way, the individual temperature sensors themselves perform local physical averaging of the temperature of the (first) heated fluid flow.

Typically the mean spacing between adjacent temperature sensors in the said distribution direction is different from the mean spacing of adjacent heating elements in the said distribution direction. For example, it may be that the mean spacing between adjacent temperature sensors in the said distribution direction is greater than the mean spacing between adjacent heating elements in the said distribution direction.

Typically adjacent temperature sensors of the said plurality of temperature sensors are offset from each other in the said distribution direction by a first distance and adjacent heating elements are offset from each other in the said distribution direction by a second distance different from the first distance.

Typically no other said temperature sensors are positioned between adjacent temperature sensors in the distribution direction. Typically no other said heating elements are positioned between adjacent heating elements in the said distribution direction.

Typically the said heating elements are distributed periodically in the said distribution direction, the said temperature sensors are distributed periodically in the said distribution direction and the period of the said heating element distribution is different from the period of the said temperature sensor distribution.

Typically the fan, the heating elements and the temperature sensors are provided within a housing (e.g. a forced fluid (e.g. air) warmer housing). Typically the said temperature sensors are offset from each other in the said distribution direction between first and second walls of the housing, the first and second walls being spaced from each other along the said distribution direction. Typically the said heating elements are offset from each other in the said distribution direction between the said first and second walls of the housing. Typically the spacing in the distribution direction between a portion of a first said temperature sensor closest to the first wall and a portion of a second said temperature sensor closest to the first wall is different from the spacing in the distribution direction between a portion of a first said heating element closest to the first wall and a portion of a second said heating element closest to the first wall, the first and second temperature sensors being adjacent to each other and the first and second heating elements being adjacent to each other.

Typically the fan comprises a plurality of blades configured to rotate about an axis to generate a fluid flow. Typically the fan is configured to receive a fluid intake (e.g. ambient air) and to generate a fluid flow having a greater velocity (typically at a greater fluid pressure, typically at a greater temperature) than the fluid intake.

Typically the heater is provided downstream of the fan (typically with respect to the principle flow direction of the heated fluid flow). Typically the heater is provided in a fluid flow path along which the fluid flow generated by the fan flows, the heater being configured to heat the said fluid flow to generate the said (first) heated fluid flow. Alternatively, it may be that the heater is provided upstream of the fan (typically with respect to the principle flow direction of the heated fluid flow).

Typically the temperature sensors are provided downstream of the heater.

It may be that the temperature sensors are provided downstream of the fan.

It may be that the temperature sensors are provided downstream of the fan and the heater.

Alternatively, it may be that the temperature sensors are provided upstream of the fan (e.g. between a heater provided upstream of the fan and the fan).

Typically the temperature sensors are provided in a fluid flow path along which the (first) heated fluid flow flows.

Typically the heating elements of the heater are aligned with each other.

Typically the temperature sensors are aligned with each other.

Typically the heating elements are aligned with each other in the said distribution direction (at least when viewed from a direction perpendicular to the said distribution direction and perpendicular to the principle flow direction). It may be that the heating elements are not aligned with each other when viewed along a direction parallel to the principle flow direction and/or along a direction parallel to the distribution direction.

Typically the temperature sensors are aligned with each other in the said distribution direction (at least when viewed from a direction perpendicular to the said distribution direction and perpendicular to the principle flow direction). It may be that the temperature sensors are not aligned with each other when viewed along a direction parallel to the principle flow direction and/or along a direction parallel to the distribution direction.

Typically the temperature sensors (typically excluding the said further temperature sensor configured to measure the temperature of the fluid intake, where provided) are mechanically coupled to each other, typically by a mechanical coupling extending between them (such as a frame or a plate). This helps to fix the positions of the temperature sensors relative to each other and relative to the heater. This helps to maintain the accuracy of any calibration weightings applied to the temperature measurements provided by the temperature sensors by the controller.

Typically the fan, heater and temperature sensors are provided as part of a forced fluid warmer (e.g. a forced air warmer). It may be that the controller is provided as part of the forced fluid warmer. Typically the said first fluid flow is internal to the forced fluid warmer. It may be that the said second fluid flow is external to the forced fluid warmer.

Preferably the temperature sensors are provided less than 30 cm, more preferably less than 20 cm, even more preferably less than 10 cm (and in some cases 5 cm or less than 5 cm) from the heater. Typically the temperature sensors are provided around 3 cm to 7 cm from the heater, preferably 4 cm to 6 cm from the heater.

A second aspect of the invention provides a (typically human) patient temperature regulation system comprising a fluid warming apparatus according to the first aspect of the invention; and a patient temperature regulation tool configured to receive an input fluid flow from the fluid warming apparatus, the said input fluid flow being derived from the said (first) heated fluid flow, and to adjust or maintain the temperature of a patient using the said received input fluid flow.

Typically the patient temperature regulation system further comprises a (typically flexible) hose configured to carry fluid from the (first) heated fluid flow to the patient temperature regulation tool. Typically the said input fluid flow received by the temperature regulation tool comprises a fluid flow output from the hose.

It may be that the patient temperature regulation tool comprises a blanket, a garment or an underbody (e.g. mattress) configured to regulate the temperature of the patient by forced convection. It may be that the patient temperature regulation tool comprises a pressure chamber having an air impermeable surface on a first side remote from the patient and an air permeable surface on a second side opposite the first side and facing the patient. It may be that the air impermeable surface has a port extending therethrough and configured to receive heated, pressurised air from the forced air warming apparatus. It may be that the air permeable surface allows the passage of air therethrough onto the patient (e.g. by way of openings or perforations).

It may be that the second heated fluid flow comprises the input fluid flow received by the temperature regulation tool, or a fluid flow derived therefrom. It may be that the controller is configured to predict a temperature of the said input fluid flow received by the patient temperature regulation tool, or a fluid flow derived therefrom, taking into account the temperature measurements measured by the temperature sensors. It may be that the controller is configured to regulate a temperature of the said input fluid flow received by the patient temperature regulation tool taking into account (e.g. responsive to) the temperature measurements measured by the temperature sensors.

Typically the forced fluid warming apparatus and the patient temperature regulation tool (e.g. a forced air warming blanket) are together configured to regulate the temperature of a (typically human) patient, typically in a surgical or medical environment (e.g. during a surgical operation or medical procedure).

It may be that the controller is configured to predict a temperature of a fluid flow derived from the said input fluid flow received by the patient temperature regulation tool taking into account the temperature measurements from the temperature sensors. In this case, the fluid flow derived from the said input fluid flow may comprise (for example) a fluid flow within the patient temperature regulation tool itself, a fluid flow underneath the patient temperature regulation tool or a fluid flow from the temperature regulation tool onto a subject (e.g. onto a (typically human) patient).

Typically the controller is configured to regulate the temperature of a patient by regulating the temperature of the input fluid flow received by the patient temperature regulation tool taking into account (e.g. responsive to) the temperature measurements from the said temperature sensors.

A third aspect of the invention provides a method of warming fluid (typically gas, typically air) comprising: generating a heated fluid flow (typically a heated air flow) having a principle fluid flow direction and an inhomogeneous temperature distribution in a distribution direction perpendicular to the principle fluid flow direction; and measuring the temperatures of a plurality of portions of the heated fluid flow offset from each other in the distribution direction, at least two (preferably at least three, preferably each) of the plurality of portions of the heated fluid flow having different temperatures.

It may be that the method further comprises providing an output taking into account (typically responsive to) the temperature measurements of the said portions of the heated fluid flow. Typically the said heated fluid flow is a first heated fluid flow and the output relates to a second heated fluid flow downstream of the first heated fluid flow (typically with respect to the principle flow direction of the heated fluid flow). For example, it may be that the output comprises a predicted temperature of the second heated fluid flow. Additionally or alternatively it may be that the output comprises a signal for regulating a temperature of the second heated fluid flow.

Accordingly, it may be that the heated fluid flow is a first heated fluid flow, and the method further comprises predicting and/or regulating a temperature of a second heated fluid flow downstream of the first heated fluid flow (typically derived therefrom, typically having a more homogeneous temperature distribution than the first heated fluid flow) taking into account the measured temperatures of the said at least two portions of the heated fluid flow.

It may be that the method comprises regulating the temperature of the second heated fluid flow by adjusting a temperature of the heated fluid flow taking into account (e.g. responsive to) the temperatures measured by the said temperature sensors (e.g. in accordance with a target temperature).

It may be that the method comprises regulating a temperature of a second heated fluid flow downstream of the first heated fluid flow taking into account (typically responsive to) the temperatures measured at at least two portions of the heated fluid flow using predetermined calibration data. For example, the predetermined calibration data may comprise a plurality of predetermined calibration data portions, each of which comprises one or more control parameters associated with temperatures measured at one or more (or each) of the said at least two portions of the heated fluid flow. It may be that the method comprises selecting a predetermined calibration data portion from the predetermined calibration data responsive to the temperatures measured at the said portions of the heated fluid flow and using the control parameter(s) from the selected predetermined calibration data portion to regulate the temperature of the second heated fluid flow.

Typically the method further comprises measuring the temperature of each said portion of the (first) heated fluid flow independently of the other portions.

Typically the step of generating a heated fluid flow comprises generating a heated fluid flow using a heater, the heater comprising a plurality of (typically electrically resistive or Joule) heating elements offset (and typically spaced) from each other in the said distribution direction.

Typically the heating elements are distributed periodically in the said distribution direction.

Typically the said plurality of portions of the (first) heated fluid flow are distributed periodically in the said distribution direction, the period of the distribution of the said portions being different from the period of the distribution of the said heating elements.

Typically the step of measuring the temperatures of a plurality of portions of the (first) heated fluid flow comprises measuring the temperatures of the said plurality of portions of the (first) heated fluid flow by way of a plurality of temperature sensors offset from each other in the distribution direction.

Typically the said temperature sensors are distributed periodically in the said distribution direction, the period of the temperature sensor distribution being different from the period of the heating element distribution.

Typically the said portions are downstream of the fan. Alternatively, the said portions are upstream of the fan. For example, it may be that the heater is upstream of the fan and the said portions are between the heater and the fan. It may be that the temperature sensors are also between the heater and the fan (i.e. upstream of the fan and downstream of the heater).

Typically the method further comprises providing the said output taking into account a fluid velocity profile (i.e. a variation in fluid velocity) of the (first) heated fluid flow (typically in the distribution direction). Typically the method comprises predicting and/or regulating the temperature of the second heated fluid flow taking into account a fluid velocity profile of the (first) heated fluid flow (typically in the distribution direction).

It may be that the method comprises predicting and/or regulating the temperature of the said second fluid flow taking into account the fluid velocity profile of the heated fluid flow by weighting the said measured temperatures in accordance with respective predetermined (e.g. calibration) weightings.

Typically the weightings applied to two or more of the measured temperatures are different from each other.

It may be that the method further comprises summing the weighted temperature measurements and divide the sum by the number of the said weighted temperature measurements summed.

It may be that the method comprises adjusting the said predetermined weightings, e.g. so as to optimise the accuracy and/or reproducibility and/or stability of a predicted temperature value or of the regulation of the temperature of the second heated fluid flow.

The method may further comprise measuring the temperature of a fluid intake (e.g. ambient air) and predicting and/or regulating the said temperature of the second fluid flow taking into account the measured temperature of the fluid intake.

The method may further comprise carrying fluid from the (first) heated fluid flow to a patient temperature regulation tool, e.g. by a hose.

Typically the said input fluid flow received by the patient temperature regulation tool comprises a fluid flow output from a hose configured to carry fluid from the (first) heated fluid flow to the patient temperature regulation tool. It may be that the second fluid flow comprises the input fluid flow received by the patient temperature regulation tool, or an air flow derived therefrom.

Although various aspects and embodiments of the present invention have been described separately above, any of the aspects and features of the present invention can be used in conjunction with any other aspect, embodiment or feature where appropriate. For example apparatus features may where appropriate be interchanged with method features.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
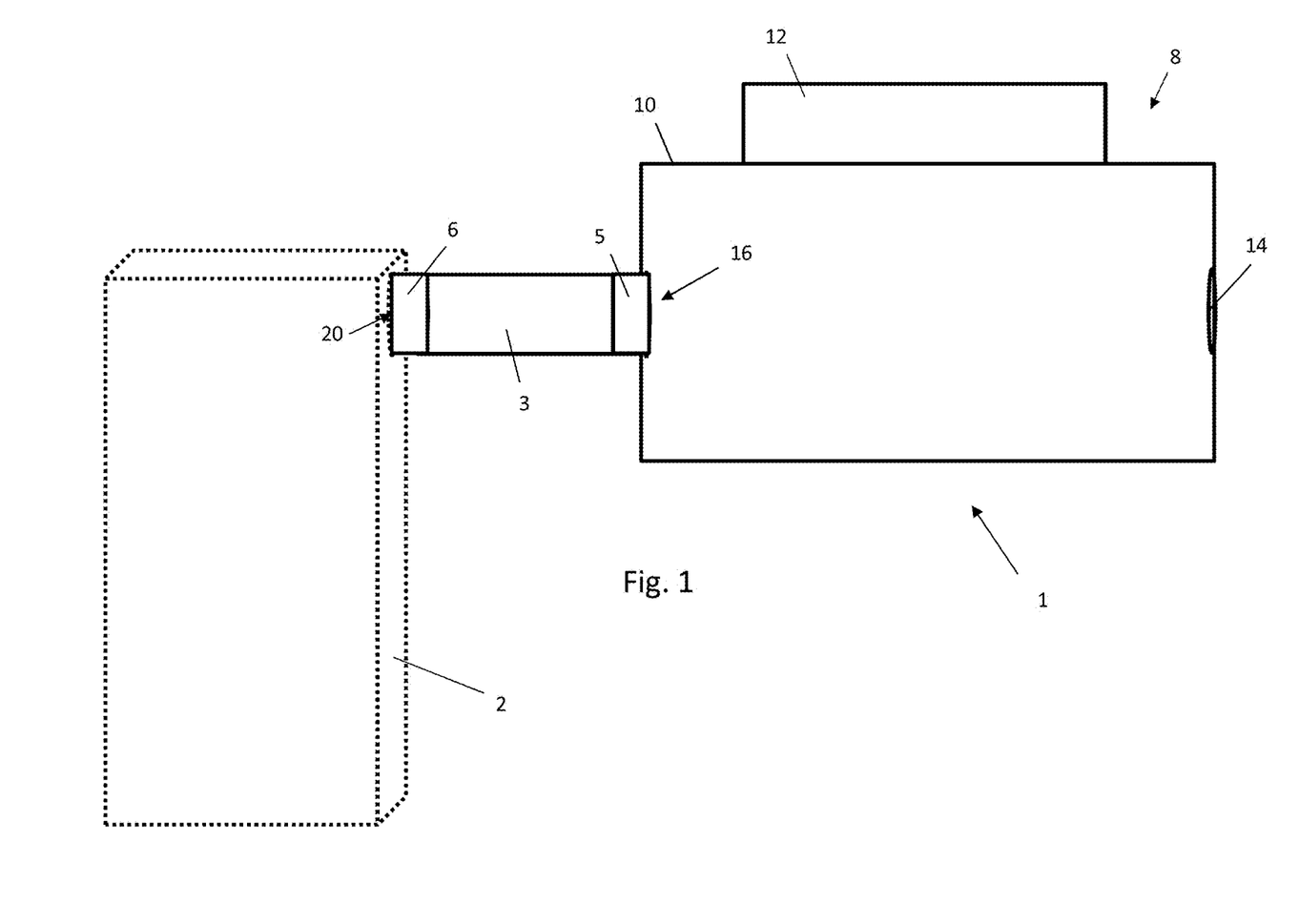
FIG. 1 is a block diagram showing a forced air warmer coupled to a perforated blanket by a flexible hose.

FIG. 1 is a block diagram showing a forced air warmer 1 fluidly coupled to a perforated blanket 2 by a flexible hose 3, the perforated blanket 2 being draped over a (typically human) patient (not shown) during a medical procedure or operation (typically when the patient is under a general anaesthetic). Air heated by the forced air warmer 1 is delivered to the blanket 2 through the hose 3. The blanket 2 contains a plurality of perforations (not shown) through which heated air received from the forced air warmer 1 is delivered to the patient to heat the patient by forced convection, thereby preventing the onset of unintentional hypothermia in the patient.

Figure 2:
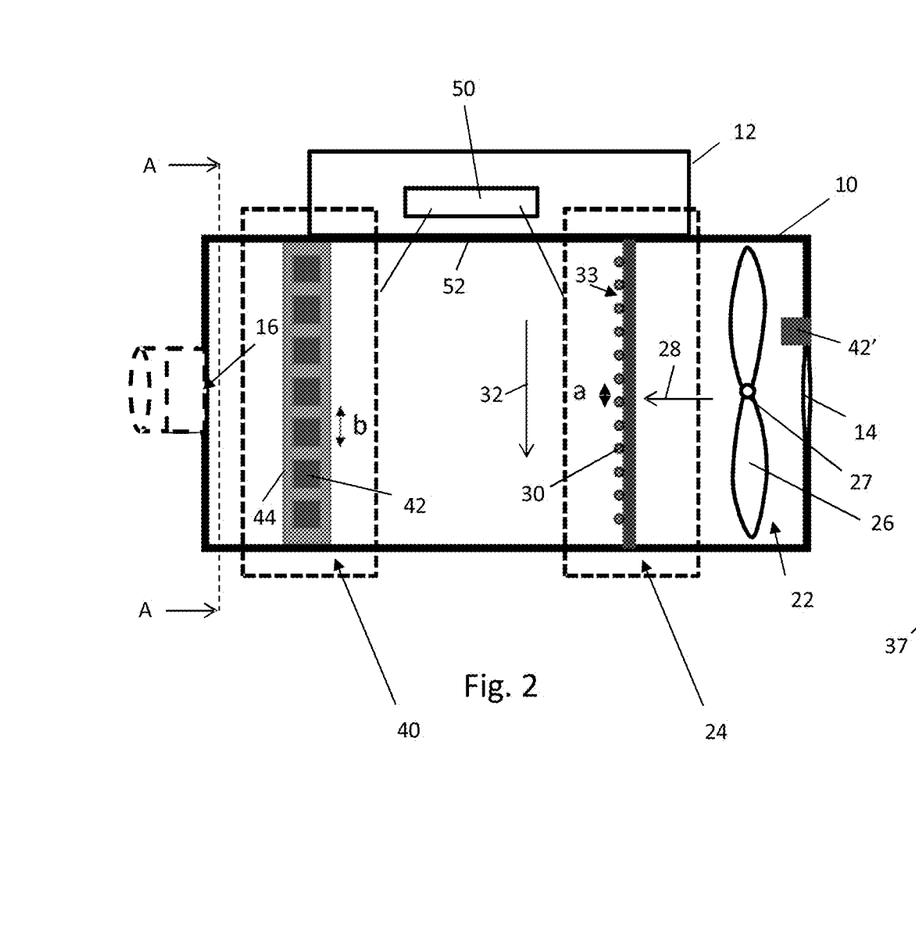
FIG. 2 is a block diagram showing a fan, a heater, a temperature measurement module and a controller of the forced air warmer of FIG. 1.

As shown in both FIGS. 1 and 2, the forced air warmer 1 comprises a housing 8 having a first hollow, cylindrical portion 10 (although it will be understood that the first housing portion 10 is not necessarily cylindrical) and a second portion 12 coupled to (or integrally formed with) the first portion 10, the first portion 10 comprising an air intake port 14 through which ambient air can be received into the first portion 10 and an outlet port 16 through which ambient air which has been heated by the forced air warmer 1 can be output to the hose 3. The flexible hose 3 is coupled to the outlet port 16 of the forced air warmer 1 by a first coupler 5 and to an inlet port 20 of the perforated blanket 2 by a second coupler 6.

As shown in FIG. 2, the first portion 10 of the housing 8 also houses a fan 22 and a heater 24 positioned downstream of the fan 22, the fan 22 and the heater 24 being together configured to generate a heated air flow by heating ambient air received into the first housing portion 10 through the air intake port 14. The fan 22 comprises a plurality of blades 26 which rotate about an axis 27 to generate an air flow towards the heater 24, the air flow having a principle direction of flow parallel to a longitudinal axis of the first housing portion 10 and being indicated in FIG. 2 by an arrow 28.

Figure 3:
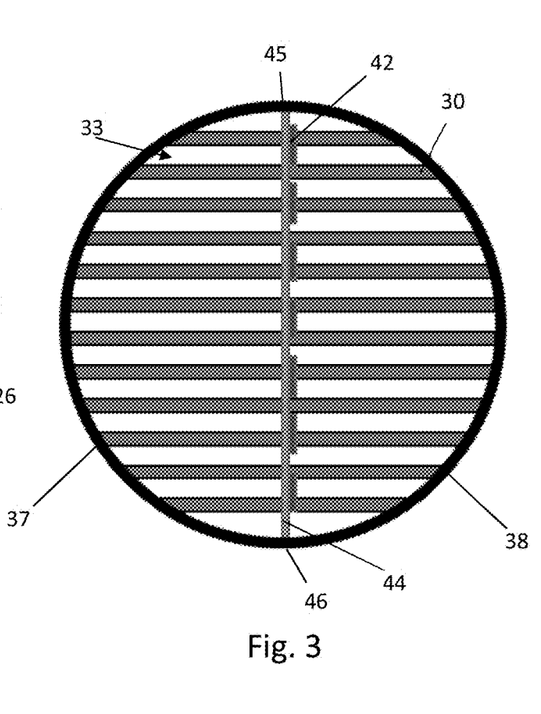
FIG. 3 is a sectional view of the first portion of the housing of the forced air warmer of FIGS. 1 and 2 along the line A-A indicated in FIG. 2, FIG. 3 showing the heater and the temperature measurement module of the forced air warmer (the fan is omitted from this view)

The heater 24 comprises twelve electrically resistive (or Joule) heating elements 30 (although it will be understood that any suitable number of heating elements may be provided) offset and spaced from each other along a distribution direction (which distribution direction is indicated by arrow 32 in FIG. 2) such that there are gaps 33 between them, the distribution direction 32 being perpendicular to the principle direction of flow 28. Each of the heating elements 30 consists of an electrically conductive wire extending across the first portion 10 of the housing 8 in a direction perpendicular to the principle direction of flow 28, and perpendicular to the distribution direction 32, between opposing inner walls 37, 38 of the said first portion 10 of the housing 8 (see FIG. 3). The heating elements 30 are distributed periodically along the distribution direction 32 having a period "a" as shown in FIG. 2 (the period "a" being a measurement of the periodicity of a repeating pattern of the heating elements 30 along the distribution direction 32, being shown in FIG. 2 as extending from a lower surface of one of the heating elements 30 and the lower surface of the adjacent (neighbouring) heating element 30). The air flow generated by the fan 22 flows onto the heating elements 30 and through the gaps 33 between the heating elements towards the outlet port 16.

The first portion 10 of the housing 8 also houses a temperature measurement module 40 positioned downstream of the fan 22 and the heater 24 in a fluid flow path along which the heated air flow generated by the fan 22 and the heater 24 flows before entering the hose 3. The temperature measurement module 40 comprises seven (although it will be understood that any suitable number may be provided) temperature sensors 42 (typically thermistors configured to measure temperature by detecting a temperature dependent change in electrical resistance of a material, but any suitable temperature sensor could be used) mechanically coupled to each other by a plate 44 extending between upper and lower walls 45, 46 of the first portion 10 of the housing 8, the temperature sensors 42 being offset and spaced from each other along the plate in the said distribution direction 32. The temperature sensors 42 are aligned with each other in the distribution direction 32, but they need not be. For example, they may be offset from each other in a direction perpendicular to the distribution direction 32 and perpendicular to the principle direction of flow 28 (i.e. into or out of the view of FIG. 2). In this case, the temperature sensors 42 are still typically aligned with each other along the distribution direction 32 when viewed along a direction perpendicular to the distribution direction 32 and perpendicular to the principle flow direction 28 (i.e. when viewed as shown in FIG. 2), although again they need not be. As shown in FIG. 2, the temperature sensors 42 have a greater extent in the distribution direction 32 than the heating elements 30. By providing the temperature sensors 42 with a greater extent in the distribution direction than the heating elements 30, the individual temperature sensors themselves cover both relatively warmer and relatively cooler portions of the heated air flow, thereby providing local physical averaging of the temperature of the heated air flow along the distribution direction (although it will be understood that this is not necessary). In addition, the temperature sensors 42 are distributed periodically along the plate 44, the distribution of the temperature sensors 42 in the distribution direction 32 having a different period "b" from that ("a") of the heating elements 30 in that direction (the period "b" being a measurement of the periodicity of a repeating pattern of the temperature sensors 42 along the distribution direction 32, shown in FIG. 2 as extending from a lower surface of one of the temperature sensors 42 to the lower surface of the adjacent (neighbouring) temperature sensor 42). Each of the temperature sensors 42 is configured to measure a respective temperature of the air flow individually (i.e. independently of the other temperature sensors 42).

The second housing portion 12 houses a controller 50 which is in (typically wired) electrical communication with the heating elements 30 and the temperature sensors 42. The second housing portion 12 is fluidly segregated from the first housing portion 10 by a wall 52 which prevents heated air from the heated air flow generated by the fan 22 and the heater 24 from coming into contact with the controller 50, although wires typically extend through sealed openings in the wall 52 between the controller 50 and the heating elements 30 and the temperature sensors 42 so as to bring them into communication with the controller 50. However, it will be understood that the fan 22, heater 24, temperature measurement module 40 and controller 50 may alternatively be provided in the same housing portion.

The controller 50 typically comprises a digital computer processor implementing a computer software program (e.g. a microcontroller), but it will be understood that the controller 50 could alternatively be implemented in analog electronics (for example) or that the controller 50 could alternatively comprise more than one computer processor (e.g. a first computer processor for controlling the heat output by the heater 24 and a second computer processor for controlling a speed of the fan 22). The controller 50 is typically in communication with a user interface (not shown) provided on the upper surface of the second housing portion 12, which a user can use to set a desired patient temperature regulation regime to be implemented by the controller 50 by way of control signals transmitted to the heating elements 30 to regulate the temperature of the heated air flow generated by the heater 24 and the fan 22, the control signals being determined by the controller 50 responsive to temperature measurements received by the controller 50 from the temperature sensors 42 of the temperature measurement module 40 and responsive to the user controlled temperature regulation regime (which may specify one or more target temperatures of the air flow or of the patient over time).

Air which contacts the heating elements 30 is heated; the air which flows through the gaps 33 between heating elements 30 without contacting the heating elements 30 remains relatively unheated, although some heating by thermal radiation will take place. Accordingly, close to the heater 24, the heated air flow generated by the fan 22 and the heater 24 is laminar, containing alternate layers of relatively hot and relatively cool fluid flow portions along the distribution direction 32, thereby providing the heated air flow with an inhomogeneous temperature distribution along the distribution direction 32. As the air flows along the first portion 10 of the housing 8 in the principle flow direction 28, through the hose 3 and into the blanket 2, the heated air flow mixes so that it has a substantially homogeneous temperature distribution by the time it is incident on the patient.

The temperature measurement module 40 is positioned close to (typically less than 30 cm, more typically less than 20 cm, even more typically less than 10 cm from) the heater 24 in order to be able to be able to quickly detect changes in the temperature of the heated air flow generated by the heater 24 and the fan 22. However, as discussed above, the heated air flow incident on the temperature measurement module 40 has an inhomogeneous temperature distribution along the distribution direction 32. The temperature measurements made by the individual temperature sensors 42 are therefore not themselves typically indicative of the temperature of the air flow incident on the patient. Accordingly, the controller 50 is configured to receive temperature measurements from each of the temperature sensors 42 of the temperature measurement module 40 and to provide an output dependent on the temperature measurements received from the temperature sensors 42.

Typically the controller 50 is configured to predict the temperature of the input air flow received by the blanket 2 from the hose 3 (which is derived from the heated air flow generated by the fan and the heater), or of an air flow derived from the air flow received by the blanket 2 from the hose 3 (e.g. an air flow within the blanket itself or an air flow underneath the blanket, for example an air flow from the blanket onto the patient) by processing the received temperature measurements. It may be that the controller 50 is configured to output an indication (e.g. a visual indication) of the predicted temperature on the user interface. Additionally or alternatively, the controller 50 may be configured to regulate the temperature of the input air flow received by the blanket 2 taking into account the received temperature measurements. The temperature sensors 42 are positioned such that, due to the inhomogeneous temperature distribution, the temperatures measured by at least two (more typically at least three, even more typically each) of the temperature sensors 42 will be different.

It will be understood that, because the periodicity "b" of the spacing of the temperature sensors 42 is different from the periodicity "a" of the spacing of the heating elements 30 along the distribution direction 32, it is ensured that at least some (typically each) of the temperature sensors 42 measure the temperatures of respective portions of the heated air flow which have different temperatures from each other. This helps to ensure that the temperature measurements take into account portions of the heated air flow which have been in contact with heating elements 30 and portions of the heated air flow which have not been in contact with heating elements 30, thereby providing temperature measurement data more indicative of the temperature of the heated air flow as a whole.

Generally, the more temperature sensors 42 provided which measure portions of the heated air flow having different temperatures, the more complete the temperature measurement data, the more accurate the predicted temperature value determined by the controller 50 and the better regulated the temperature of the air flow received by the blanket 2. A minimum of two temperature sensors 42 can be provided, e.g. one for measuring the temperature of a portion of the air flow which has been heated by a heating element 30 and another for measuring the temperature of a portion of the air flow which has been relatively unheated (at least directly) by a heating element 30.

By measuring the temperature of the heated air flow generated by the heater 24 and the fan 22 at a plurality of positions along the distribution direction where the air flow has different temperature, a temperature can be predicted which is reliably indicative of the temperature of the air flow incident on the patient without having to wait for the air flow to physically mix and the temperature of the temperature in the blanket 2 can be better regulated. Indeed, the relevant processing is performed by the controller 50 far more quickly than it takes for the air flow to physically mix in order to achieve a homogeneous temperature distribution. In addition, because the temperature measurement module 40 can be provided close to the heater 24, it can quickly detect changes in the temperature of the heated air flow generated by the heater 24 and the fan 22. Thus, the arrangement shown in FIGS. 1 to 3 allows changes in the temperature of the heated air flow generated by the fan 22 and the heater 24 to be quickly and accurately detected, thereby allowing the controller 50 to quickly adjust the temperature of the air flow received by the blanket 2 if required (e.g. by changing the power supplied to the heating elements 30), thereby allowing a heated air flow of accurately controlled and stable temperature to be supplied to the patient.

It will be understood that the temperature of the air flow received by the blanket 2 need not itself be calculated by the controller 50 (although it may be), but the temperature measurements from the temperature sensors 42 can still be used by the controller to regulate the temperature of the air flow received by the blanket 2 (e.g. by use of a look-up table associating temperature measurements with heater and/or fan control settings to be implemented by the controller 50).

When the heated air flow flows through the hose 3, the ambient temperature of the environment external to the hose 3 typically affects the rate of cooling of the heated air flow before it is received by the blanket 2 and before it is incident on the patient. Accordingly, a further temperature sensor 42' (see FIG. 2) is typically provided adjacent to the intake port 14 which is configured to measure the temperature of the ambient air which is input to the air warmer 1 through the intake port 14. The temperature sensor 42' is also provided in (typically wired, but in some embodiments wireless) communication with the controller 50 such that the controller 50 receives measurements of the ambient temperature from the temperature sensor 42'. It may be that the controller 50 is configured to predict and/or regulate the temperature of the input air flow received by the blanket 2 from the hose 3, or an air flow derived therefrom (e.g. a temperature of the heated air flow incident on the patient from the blanket 2), taking into account the ambient temperature measured by the temperature sensor 42'. It will be understood that the controller 50 may also take into account other parameters, such as the length of the hose 3 which may be input be a user, or which may be a standard fixed value. It may be that the controller 50 is configured to regulate the temperature of the heated air flow generated by the fan 22 and the heater 24 responsive to the predicted temperature of the input air flow received by the blanket 2 (or of the air flow derived therefrom).

Figure 4:
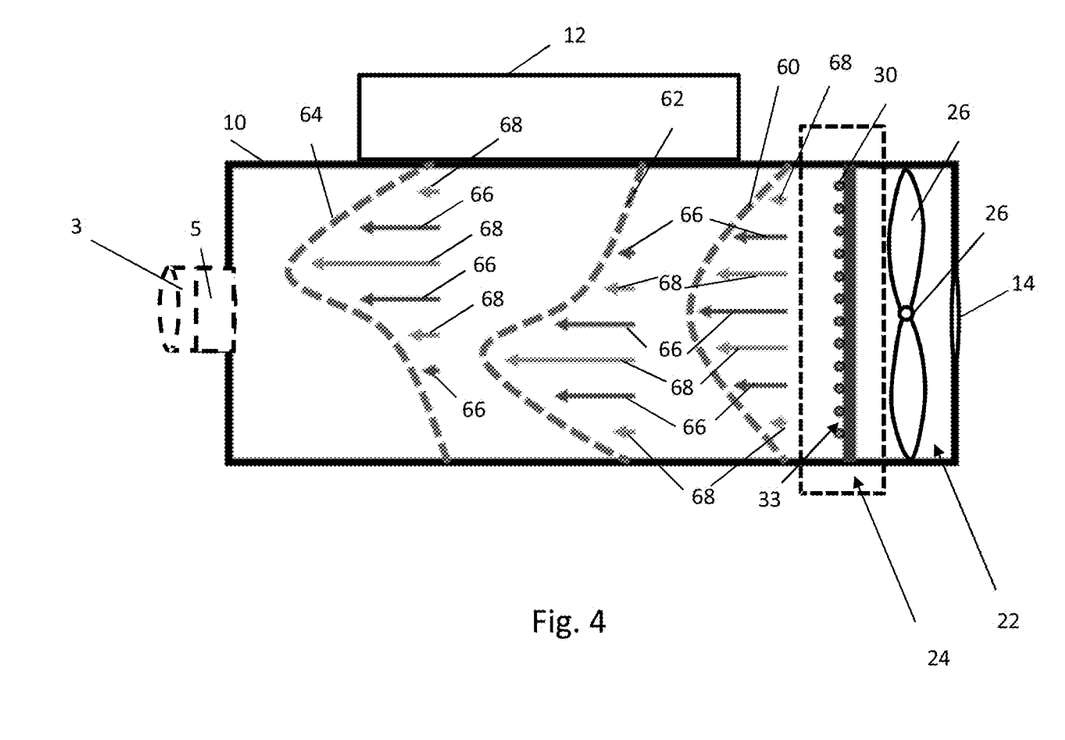
FIG. 4 is the block diagram of FIG. 2 but omitting the temperature measurement module and showing different possible air velocity profiles of the air flow generated by the heater and the fan of the forced air warmer.

The air velocity profile around the heater 24 depends on the shape of the heater 24, the hose 3 and the housing 8. Three exemplary alternative air velocity profiles 60-64 are illustrated in FIG. 4 (in which the temperature measurement module 40, the controller 50 and the temperature measurement sensor 42' are omitted), with arrows labelled 66 indicating relatively warm portions of the air velocity profiles and arrows labelled 68 indicating relatively cool portions of the air velocity profiles. In the first exemplary air velocity profile 60, the air flow is strongest at a portion of the air flow flowing along the middle of the first portion 10 of the housing 8 (with respect to the distribution direction 32), progressively reducing in strength towards the top and bottom of the first portion 10. In the second exemplary air velocity profile 62, the air flow is strongest at an intermediate portion between the bottom of the first portion 10 of the housing 8 and the middle of the first portion 10, reducing in strength significantly towards the top and bottom of the first portion 10. In the third exemplary air velocity profile 64, the air flow is strongest at an intermediate portion between the top of the first portion 10 of the housing 8 and the middle of the first portion 10, progressively reducing in strength towards the top and bottom of the first portion 10. Temperatures of the air where the air flow velocity is lower are less relevant to the temperature of the heated air flow incident on the patient than temperatures of the air flow where the air velocity is greater. In addition, it is typically difficult to predict how the air flow velocity will vary along the distribution direction 32. Accordingly, to manage the difficulty in predicting the air velocity profile around the heater 24, an adjustable weighting factor can be applied by the controller 50 to the temperature measurements measured by the individual temperature sensors 42. Typically greater weighting factors are applied to the temperature measurements made by temperature sensors 42 in regions of the flow having greater air flow velocities, so that the temperature measurements at those points are given greater significance by the controller 50 than temperature measurements made in regions of lower air flow velocity (given that they will contribute more to the temperature of the air flow received by the blanket 2). As the air flow velocity profile is difficult to predict, the weighting values can be tuned experimentally to optimise the accuracy, reproducibility and stability of the temperature values predicted (and or temperature regulation signals output) by the controller 50 from the temperature measurements from the temperature measurement module 40. By taking into account the fluid velocity profile, the controller 50 can better predict and regulate the temperature of the air flow received by the blanket 2.

It will be understood that the fluid velocity profile changes as the fluid flows downstream towards the blanket on account of the air flow physically mixing. Accordingly, the fluid velocity profile along the distribution direction will depend on the physical position of the temperature measurement module 40. In addition, because the temperature sensors 42 have a temperature sensitive portion which has a finite extent in the distribution direction, some of the variations in fluid velocity along the distribution direction will be physically averaged by the temperature sensors themselves. This can be accounted for in the (typically different) weightings applied to the temperature measurements obtained from the individual temperature sensors 42 by the controller 50.

Figure 5:
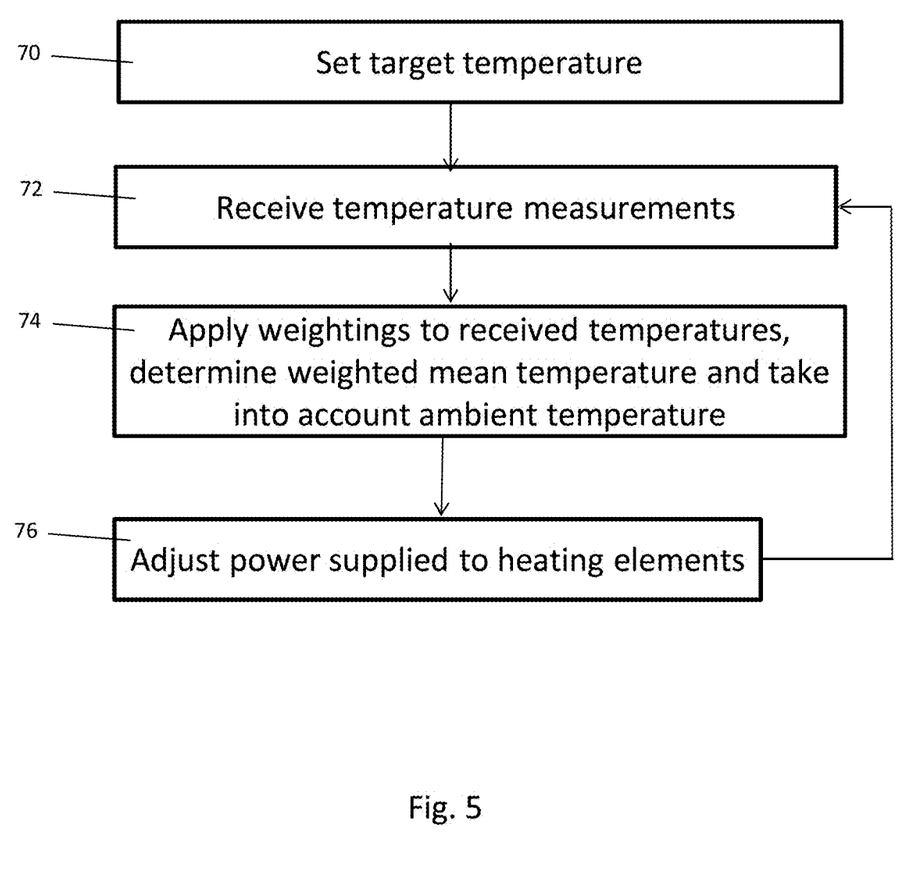
FIG. 5 is a flow chart of an exemplary algorithm executed by the controller of the forced air warmer.

FIG. 5 is a flow chart illustrating an example of an algorithm performed by the controller 50 to adjust the output of the heating elements 30 responsive to the temperature measurements made by the temperature sensors 42, 42' and to a target temperature set by a user (e.g. medical practitioner). In a first step 70, the user (e.g. medical practitioner) sets a target temperature using the user interface on the housing 8. In a next step 72, the controller 50 receives temperature measurements from the temperature sensors 42, 42'. Then, in step 74, the controller 50 multiplies the received temperature measurements from the temperature sensors 42 by respective predetermined calibration weightings, sums the weighted temperature measurements and divides the sum by the number of temperature sensors (in this case seven) to determine a weighted mean temperature of the heated fluid flow generated by the fan 22 and the heater 24. In step 74, the controller 50 predicts a temperature of the input fluid flow received by the blanket 2 from the hose 3 (or of an air flow derived therefrom) taking into account the said weighted mean temperature and the temperature measurement received from the temperature sensor 42' at the air intake port 14. In step 74, the controller 50 may further take into account other factors which will affect the temperature of the input air flow received by the blanket 2 (or of an air flow derived therefrom), such as the length of the hose 3 in combination with the temperature of the external environment in which the hose is provided and/or thermal and/or physical properties of the blanket 2. In a next step 76, the power supplied to the heating elements 30 is adjusted to bring the predicted temperature closer to the target temperature. Next, the algorithm returns to step 72. If the medical practitioner adjusts the target temperature, the algorithm returns to step 70.

Further variations and modifications may be made within the scope of the invention herein described. For example, it is not necessary for the temperature sensors 42 or heating elements 30 to be spaced periodically along the distribution direction 32, so long as the temperature sensors 42 are configured to measure temperatures of respective portions of the heated air flow having different temperatures from each other. As another example, it is not necessary for the heater 24 to be provided downstream of the fan 22. For example, the heater 24 may be provided upstream of the fan 22. In this case, it may be that the temperature measurement module 40 is provided between the heater 24 and the fan 22 (i.e. it may be that the temperature measurement module 40 is provided downstream of the heater but upstream of the fan).

The fluid warming apparatus may also comprise a safety temperature sensor configured to measure a temperature of the heated fluid flow to provide a safety temperature measurement. The fluid warming apparatus may further comprise a safety controller (which may be the same controller 50 discussed above or, more typically, a separate controller from the controller 50) configured to receive temperature measurements from the safety temperature sensor and to reduce the output of, or switch off, the heater and/or the fan responsive to the safety temperature measurement exceeding a threshold.

The invention claimed is:

1. A fluid warming apparatus comprising:
a fan;
a heater, the fan and the heater being configured to generate a first heated fluid flow having a principal flow direction and an inhomogeneous temperature distribution in a distribution direction perpendicular to the principal flow direction;
a plurality of temperature sensors offset from each other in the distribution direction, wherein at least two of the temperature sensors are configured to measure different temperatures of respective portions of the first heated fluid flow having different temperatures; and
a controller configured to predict and/or regulate a temperature of a second heated fluid flow downstream of the first heated fluid flow taking into account a combination of the different temperatures measured by the at least two of the temperature sensors;
wherein the heater comprises a plurality of heating elements offset from each other in the distribution direction, and
the plurality of temperature sensors have a greater extent in the distribution direction than the plurality of heating elements.

2. The fluid warming apparatus according to claim 1 wherein the controller is configured to predict and/or regulate the temperature of the second heated fluid flow taking into account a variation in fluid velocity of the first heated fluid flow along the distribution direction.

3. The fluid warming apparatus according to claim 2 wherein the controller is configured to predict and/or regulate the temperature of the second heated fluid flow taking into account a variation in the fluid velocity of the first heated fluid flow along the distribution direction by weighting the different temperatures measured by the temperature sensors in accordance with respective predetermined weightings.

4. The fluid warming apparatus according to claim 3 wherein the controller is further configured to sum the weighted temperature measurements and divide the sum by the number of temperature sensors.

5. The fluid warming apparatus according to claim 1 further comprising at least one further temperature sensor configured to measure a temperature of a fluid intake, wherein the controller is further configured to predict and/or regulate the temperature of the second heated fluid flow taking into account the measured temperature of the fluid intake.

6. The fluid warming apparatus according to claim 1 wherein the controller is configured to regulate the temperature of the second heated fluid flow by adjusting one or more properties of the heater and/or one or more properties of the fan taking into account the different temperatures measured by the temperature sensors.

7. The fluid warming apparatus according to claim 1 further comprising a hose in fluid communication with the first heated fluid flow, wherein the second heated fluid flow is carried by the hose or provided downstream of the hose.

8. The fluid warming apparatus according to claim 1 wherein each of the temperature sensors is configured to measure the temperature of the respective portion of the first heated fluid flow independently of the other temperature sensor(s).

9. The fluid warming apparatus according to claim 1 wherein the temperature sensors are distributed in the distribution direction differently from the distribution of the heating elements in the distribution direction.

10. A patient temperature regulation system comprising: a fluid warming apparatus according to claim 1; and a patient temperature regulation tool configured to receive an input fluid flow from the fluid warming apparatus, the input fluid flow being derived from the first heated fluid flow, and to adjust or maintain the temperature of a patient using the received input fluid flow.

11. The patient temperature regulation system according to claim 10 wherein the controller of the fluid warming apparatus is further configured to regulate the temperature of a patient by regulating the temperature of the input fluid flow received by the patient temperature regulation tool taking into account the temperature measurements from the temperature sensors.

12. The fluid warming apparatus according to claim 1 wherein a determination of the combination of the different measured temperatures of at least two portions of the heated fluid flow includes determining a weighted mean of the different measured temperatures.

13. The fluid warming apparatus according to claim 1, wherein:
the plurality of temperature sensors are distributed periodically in the distribution direction with a different period from that of the plurality of heating elements in the distribution direction; and
the period is a measurement of periodicity of a repeating pattern of the plurality of temperature sensors along the distribution direction.

14. The fluid warming apparatus according to claim 1, wherein the plurality of heating elements are aligned linearly along the distribution direction.

15. The fluid warming apparatus according to claim 1, wherein the plurality of temperature sensors comprises at least three temperature sensors aligned linearly along the distribution direction.

16. The fluid warming apparatus according to claim 1, wherein the plurality of temperature sensors form a temperature measurement module positioned less than 30 cm from the heater.

17. A method of warming fluid comprising:
generating a first heated fluid flow having a principal fluid flow direction and an inhomogeneous temperature distribution in a distribution direction perpendicular to the principal fluid flow direction;
measuring the temperatures of at least two portions of the first heated fluid flow offset from each other in the distribution direction using a plurality of temperature sensors offset from each other in the distribution direction, the at least two portions of the first heated fluid flow having different temperatures, wherein generating said first heated fluid flow comprises using a heater which comprises a a plurality of heating elements offset from each other in said distribution direction; and
predicting and/or regulating a temperature of a second heated fluid flow downstream of the first heated fluid flow taking into account a combination of the different measured temperatures of the at least two portions of the heated fluid flow;
the plurality of temperature sensors have a greater extent in the distribution direction than the plurality of heating elements.

18. The method of claim 17, wherein taking into account the combination of the different measured temperatures includes determining a weighted mean of the different measured temperatures of the at least two portions of the heated fluid flow.

* * * * *